United States Patent [19]

Rosenberg

[11] 4,168,710
[45] Sep. 25, 1979

[54] BALLOON CUFF AND CATHETER ASSEMBLY

[75] Inventor: Philip Rosenberg, Glenview, Ill.

[73] Assignee: The Kendall Company, Boston, Mass.

[21] Appl. No.: 823,492

[22] Filed: Aug. 10, 1977

[51] Int. Cl.² .......................................... A61M 25/00
[52] U.S. Cl. .............................. 128/349 B; 128/246; 156/294
[58] Field of Search ............... 128/348–351, 128/325, 344, 246; 156/291, 294, 295

[56] References Cited

U.S. PATENT DOCUMENTS

| 2,481,488 | 9/1949 | Auzin | 128/349 B X |
| 3,397,102 | 8/1968 | Schraub | 156/295 X |
| 3,565,079 | 2/1971 | Jackson | 128/351 |
| 3,640,282 | 2/1972 | Kamen et al. | 128/351 |
| 3,734,100 | 5/1973 | Walker et al. | 128/351 |
| 3,832,253 | 8/1974 | DiPalma et al. | 128/349 B X |
| 3,847,694 | 11/1974 | Stewing | 156/295 |
| 3,884,242 | 5/1975 | Bazell et al. | 128/349 B X |
| 4,003,382 | 1/1977 | Dyke | 128/349 B |

Primary Examiner—Dalton L. Truluck
Attorney, Agent, or Firm—Allegretti, Newitt, Witcoff & McAndrews

[57] ABSTRACT

A cuff member for a catheter assembly has grooves formed on the wall thereof to receive an adhesive for securing the cuff member to the tube of the catheter assembly.

9 Claims, 5 Drawing Figures

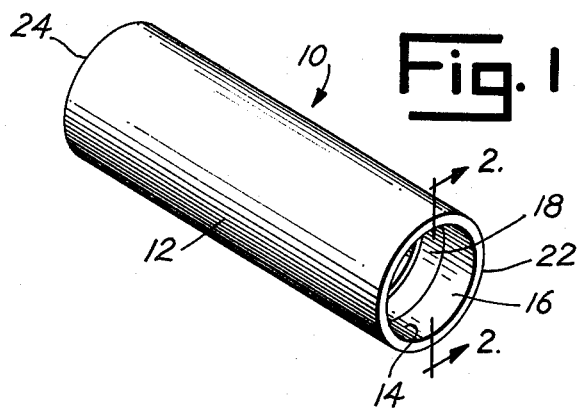
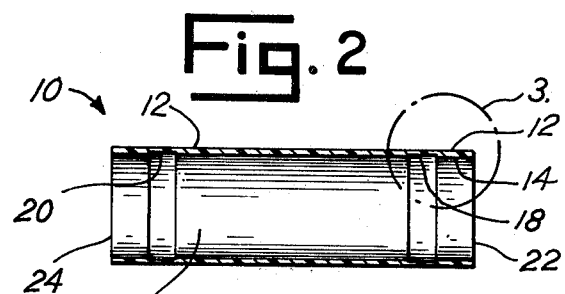
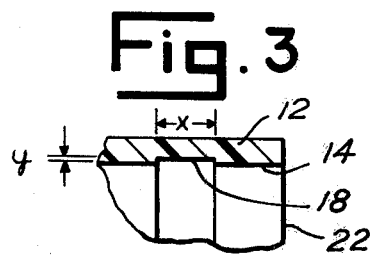
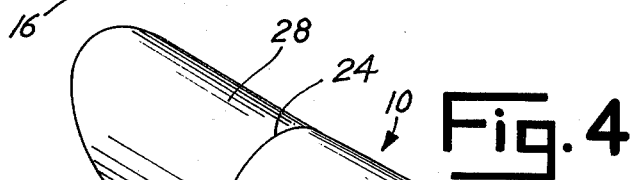
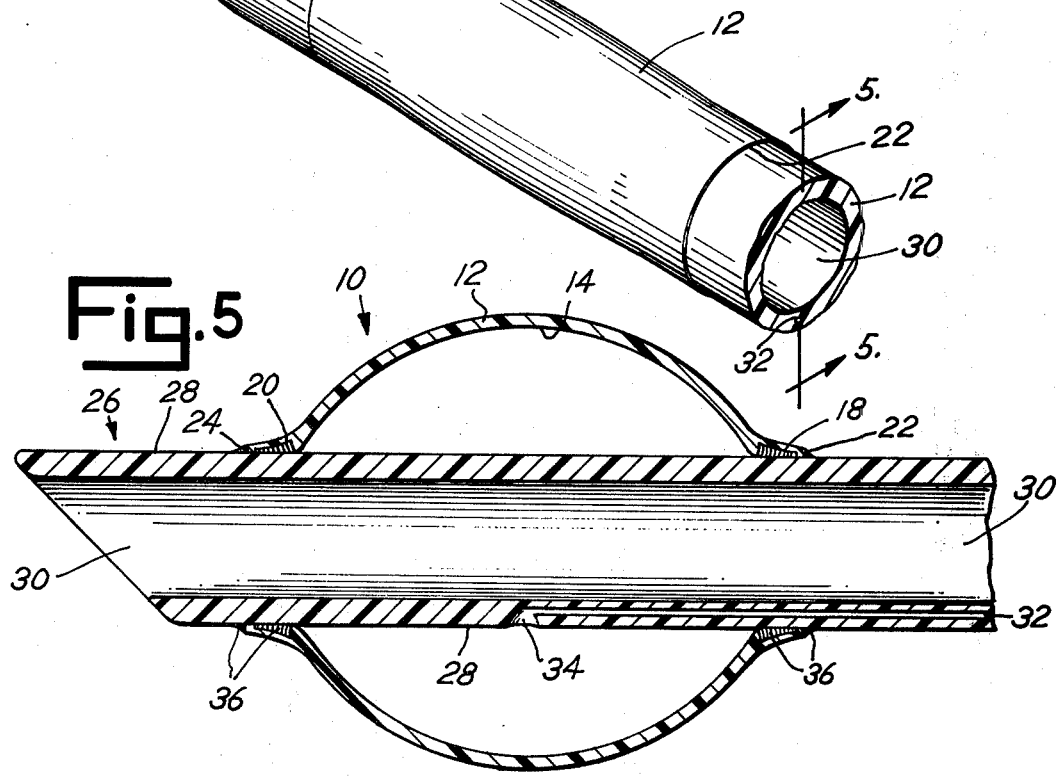

BALLOON CUFF AND CATHETER ASSEMBLY

BACKGROUND OF THE INVENTION

This invention is directed to an improved catheter balloon, or cuff member, and catheter assembly. Catheters are basic medical tools used for the input or withdrawal of fluids from the body of a patient. They generally include an inflatable balloon cuff mounted near the distal end of the catheter for retention and/or sealing purposes.

The expansible cuff or balloon is a short tubular member of a highly elastic material. The cuff is sealingly attached to the outer surface of the catheter tube by an adhesive.

When the cuff is inflated, the stretched state of the elastic material creates a force tending to peel the cuff off the catheter tube. Peeling ultimately destroys the cuff seal thereby rendering the catheter inoperative.

Various structures and procedures have been utilized to overcome the peeling problem. As shown in U.S. Pat. Nos. 3,734,100 and 3,884,242, one alternative is a thick layer of adhesive which distributes the peeling force over the entire cuff-tube interface, thereby resisting separation.

To maintain the adhesive in a relatively thick layer and to avoid a raised portion or lump on the catheter, the catheter tube must be grooved. Since catheter tubes are generally stock material, each tube must be worked, or machined, to provide a pair of annular recesses for receipt of the adhesive. This substantially increases the cost and time of manufacture.

SUMMARY OF THE INVENTION

In a principal aspect, the present invention is an improved cuff or balloon of the type secured to a catheter tube with an adhesive material. The cuff member is an elastic material having a substantially cylindrical shape. The wall of the cuff member has a pair of grooves formed therein near each end.

The grooves provide a recess for receipt of the adhesive. The grooves substantially avoid spreading of the adhesive during curing such that the necessary thickness of adhesive is maintained. The grooves also result in a uniform and smooth catheter contour.

It is thus an object of the present invention to provide an improved cuff balloon for a catheter. Another object is an improved cuff balloon having grooves for receipt of an adhesive.

A further object of the present invention is a grooved cuff member wherein the grooves are dimensioned to provide a sufficiently thick layer of adhesive and thereby avoid separation under normal operating conditions. It is also an object of the present invention to provide a cuff and catheter tube assembly which eliminate need for a groove in the catheter tube.

Another object of the present invention is to provide a cuff for catheter assemblies having grooves formed therein which define an expansible portion of the cuff and provide a cylindrical cuff surface in an assembled state. Still another object is to provide a cuff which facilitates construction of catheter assemblies.

These and other objects, advantages and features of the present invention are set forth in the detailed description which follows.

BRIEF DESCRIPTION OF THE DRAWING

In the detailed description which follows, reference will be made to the drawing wherein:

FIG. 1 is a perspective view of a preferred embodiment of the present invention;

FIG. 2 is a cross-sectional view of the cuff of FIG. 1 taken along line 2—2;

FIG. 3 is an enlarged view of the portion of FIG. 2 encircles 3;

FIG. 4 is a perspective view of a catheter assembly incorporating the cuff of FIG. 1, shown in a deflated condition; and FIG. 5 is a cross-sectional view of the catheter assembly of FIG. 4 taken along line 5—5, showing the cuff in an inflated condition.

DESCRIPTION OF THE PREFERRED EMBODIMENT

Referring to FIGS. 1-3, a preferred embodiment of the present invention is shown as a cuff member, generally designated 10. The cuff 10 is an elastic material such as silicone rubber, latex, polyvinylchloride or other similar materials, formed using commonly known compression molding or injection molding techniques. The cuff 10 includes a thin wall 12 having a smooth, substantially cylindrical shape and an inner wall surface 14. The inner wall surface 14 defines a central passage 16 extending longitudinally through the cuff 10.

The cuff 10 also includes a pair of grooves 18, 20, formed on the inner wall surface 14, near a first end 22 and second end 24, respectively, of the thin wall 12. Preferably, the grooves 18, 20 are substantially identical, substantially annular and have a predetermined width, X, and depth, Y, as shown in FIG. 3.

Referring now to FIGS. 4 and 5, the cuff member 10 is incorporated into a catheter assembly 26 by mounting thereof on a catheter tube 28. The catheter tube 28 is an elongated cylindrically-shaped, tubular member, having a central passage or lumen 30 and inflation lumen 32. The inflation lumen 32 terminates, at one end, in an inflation opening 34. The catheter tube 28 is generally extruded from a hard material relative to the material of the cuff 10.

The cuff 10 is secured to the catheter tube 28 by an adhesive material 36 substantially within the grooves 18, 20. As best shown in FIGS. 3 and 5, the configuration of the adhesive 36 is primarily determined by the width and depth of the grooves 18, 20. The width and depth of the grooves 18, 20 are empirical determinations dependent primarily on the strength and elasticity of the adhesive 36. The grooves 18, 20 and the adhesive layer formed therein must be dimensioned to distribute the strain exerted during and after inflation and to maintain the integrity of the seal between the cuff 10 and tube 28.

A suitable adhesive is SWS 951 brand adhesive, manufactured by Stauffer-Wacker Chemical Co. Utilizing this adhesive, the minimum depth of the grooves 18, 20 is approximately three one-thousands (0.003) of an inch. The preferred depth is six one-thousands (0.006) of an inch. Minimum groove width is approximately three (3) times the groove depth, or nine one-thousands (0.009) of an inch, and preferably the width is approximately ninety-four one-thousands (0.094) of an inch. The maximum depth and width of the grooves 18, 20 will vary with catheter type and materials, up to approximately ten one-thousands (0.010) and twenty-five one-hundreds (0.250) inches, respectively. In this preferred embodiment, the thickness of the cuff wall 12 is preferably approximately twenty one-thousands (0.020) of an inch. The overall length of the cuff 10 will vary depending upon the use of the catheter.

In constructing the catheter assembly 22, the first and second ends 22, 24 of the cuff 10 are folded to expose the grooves 18, 20. The catheter tube 28 is slid through the central passage 16 until the cuff 10 is centrally located about the inflation opening 34. So positioned, the cuff 10 defines a chamber (not shown) in communication with the inflation lumen 32.

The adhesive 36 is then applied to the catheter 24, and the cuff ends 22, 24 are unfolded, such that the adhesive 36 is channeled into the grooves 18, 20.

Spreading of the adhesive 36 is thereby substantially avoided and the resulting adhesive layer is sufficiently thick to resist normal peeling forces. The setting of the adhesive 36 bonds the cuff 10 to the tube 28. Because the adhesive 36 is substantially contained within grooves 18, 20, the catheter assembly 26 has a smooth contour, facilitating introduction into a bodily passageway. The catheter contour can be further improved by application of a bead of adhesive 36 adjacent the first and second ends 22, 24 of the cuff 10.

The above description relates to a single preferred embodiment of the invention. However, alternative configurations and modifications are possible within the scope of the invention. For example, the cuff member 10 may have more than two grooves 18, 20 or the grooves 18, 20 may have a different shape than disclosed herein. Additionally, the shape of the cuff 10 and catheter tube 28 may be varied. Therefore, the subject matter of the invention is limited only by the following claims and their equivalents.

What is claimed is:

1. In a catheter assembly including a catheter tube having a central lumen and an inflation lumen, an improved cuff comprising, in combination:
    an integral elastic member having a substantially cylindrical shape, an inner wall surface, a first end and a second end, said integral elastic member receiving said catheter tube and communicating with said inflation lumen; and
    an adhesive for securing said integral elastic member to said catheter tube;
    said integral elastic member defining a first groove and a second groove on said inner wall surface substantially adjacent said first end and said second end, respectively, said first groove having a first width and a first depth, said second groove having a second width and a second depth;
    said first groove and said second groove cooperating to define recess means for receiving said adhesive and providing adhesive layers wherein the strain exerted by inflation of said integral elastic member through said inflation lumen is substantially distributed throughout said adhesive layers to substantially avoid separation of said integral elastic member from said catheter tube, said recess means substantially avoiding the spreading of said adhesive during curing and providing a substantially smooth contour along said catheter tube and said integral elastic member.

2. The improved cuff member of claim 1 wherein said first groove and said second groove are substantially annular.

3. The catheter assembly of claim 1 wherein said improved cuff is silicone rubber.

4. The catheter assembly of claim 2 wherein said first width and said first depth are substantially equal to said second width and said second depth, respectively.

5. The catheter assembly of claim 4 wherein said first depth and said second depth are approximately 0.006 inches.

6. The catheter assembly of claim 4 wherein said first depth and said second depth are approximately 0.003 to 0.010 inches.

7. The catheter assembly of claim 6 wherein said first width and said second width are approximately three times said first depth and said second depth, respectively.

8. The catheter assembly of claim 6 wherein said first width and said second width are approximately 0.009 to 0.250 inches.

9. The catheter assembly of claim 6 wherein said first width and said second width are approximately 0.094 inches.

* * * * *